(12) United States Patent
Knappe et al.

(10) Patent No.: US 10,835,472 B2
(45) Date of Patent: *Nov. 17, 2020

(54) PROPELLANT-CONTAINING COSMETIC PREPARATIONS WITH STARCH PARTICLES AND ANIONIC POLYMER

(71) Applicant: Henkel AG & Co. KGaA, Duesseldorf (DE)

(72) Inventors: Thorsten Knappe, Schenefeld (DE); Tim Bethge, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,455

(22) Filed: Aug. 30, 2018

(65) Prior Publication Data
US 2019/0070091 A1    Mar. 7, 2019

(30) Foreign Application Priority Data
Sep. 1, 2017    (DE) .......... 10 2017 215 324

(51) Int. Cl.
| A61K 8/73 | (2006.01) |
| A61K 8/81 | (2006.01) |
| A61K 8/04 | (2006.01) |
| A61K 8/84 | (2006.01) |
| A61Q 5/02 | (2006.01) |

(52) U.S. Cl.
CPC ............. *A61K 8/732* (2013.01); *A61K 8/046* (2013.01); *A61K 8/8158* (2013.01); *A61K 8/84* (2013.01); *A61Q 5/02* (2013.01); *A61K 2800/31* (2013.01)

(58) Field of Classification Search
CPC ...... A61K 8/732; A61K 8/046; A61K 8/8158; A61K 8/84; A61Q 5/02
See application file for complete search history.

(56) References Cited

U.S. PATENT DOCUMENTS

| 4,423,199 | A * | 12/1983 | Chang ............. A61K 8/8158 526/307.6 |
| 7,455,848 | B2 * | 11/2008 | Hessefort ......... A61K 8/8158 424/401 |
| 8,105,393 | B2 * | 1/2012 | Suddaby .......... A61K 8/19 132/202 |
| 9,181,436 | B2 * | 11/2015 | Kitagawa ......... A61K 8/0241 |
| 2001/0007655 | A1 | 7/2001 | Paul et al. |
| 2003/0124155 | A1 * | 7/2003 | Yamato ............ A61K 8/44 424/401 |
| 2011/0168200 | A1 * | 7/2011 | Bourdin ........... A61K 8/0216 132/202 |

(Continued)

FOREIGN PATENT DOCUMENTS

| WO | 2011056625 A1 | 5/2011 |
| WO | 2016122827 A1 | 8/2016 |

OTHER PUBLICATIONS

Aaserud D.J et. al.; "Gel Permeation Chromatography Coupled to Fourier Transform Mass Spectrometry for Polymer Characterization"; Anal. Chem. 1999, 71, 4793-4799.

(Continued)

*Primary Examiner* — Robert A Wax
*Assistant Examiner* — Olga V. Tcherkasskaya
(74) *Attorney, Agent, or Firm* — Lorenz & Kopf, LLP

(57) ABSTRACT

The present disclosure relates to cosmetic compositions for cleaning keratin fibres. An exemplary cosmetic composition includes, in relation to the total weight of the cosmetic composition, a) a particle comprising, in relation to the total weight of the particle, from about 65 to about 99% by weight of a native and/or physically modified starch, b) an anionic polymer comprising a structural unit of formula (I), a structural unit of formula (II), and a structural unit of formula (III):

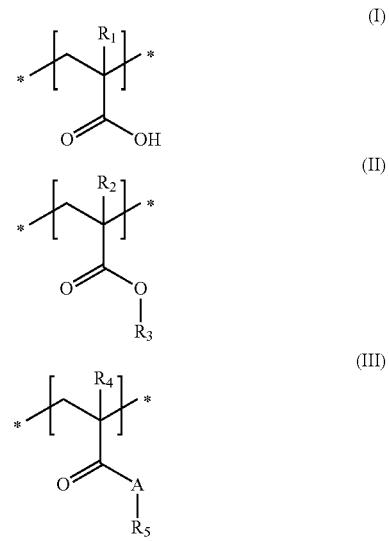

in which R1, R2 and R4, independently of one another, stand for a hydrogen atom or a C1-C4 alkyl group, R3 stands for a branched or unbranched, saturated or unsaturated C1-C12 alkyl group, R5 stands for a branched or unbranched, saturated or unsaturated C6-C14 alkyl group, and A stands for oxygen, sulfur or an NH group, and c) at least one propellant.

19 Claims, No Drawings

(56) References Cited

U.S. PATENT DOCUMENTS

2014/0076346 A1* 3/2014 Bourdin .............. A61K 8/585
　　　　　　　　　　　　　　　　　　　132/202
2014/0283865 A1* 9/2014 Avery .................. A61Q 5/02
　　　　　　　　　　　　　　　　　　　132/202

OTHER PUBLICATIONS

Neelam et al., "Various Techniques for the Modification of Starch and the Applications of its Derivatives", International Research Journal of Pharmacy, Review Article, 2012, 3 (5), pp. 25-31, Bareilly, India.

* cited by examiner

PROPELLANT-CONTAINING COSMETIC PREPARATIONS WITH STARCH PARTICLES AND ANIONIC POLYMER

CROSS-REFERENCE RELATED APPLICATION

This application claims priority to German Patent Application No. 10 2017 215 324.5, filed Sep. 1, 2017, which is incorporated herein by reference in its entirety.

TECHNICAL FIELD

The application pertains to the technical field of cleaning of keratin-containing materials, in particular human hair. The subject of the application is constituted by cosmetic agents containing at least one specific starch particle, at least one specific anionic polymer, and at least one propellant. Further subjects of the present application are constituted by methods for cleaning hair with use of these agents, and the use of these agents for cleaning keratin fibres.

BACKGROUND

The cleaning of keratin-containing fibres is generally performed on the basis of the combined effect of water, soap and mechanical work on the fibres. For example, when washing hair, a surfactant-containing shampoo is firstly applied to the damp hair and is massaged into the hair. If the hair is then rinsed with water, the contaminants detached from the hair by the water, the shampoo and/or the mechanical action are rinsed out, and the hair is cleaned in this way.

If there is no water available for cleaning hair, or if conventional hair washing is not possible due to time restraints, hair cleaning by employing a dry shampoo is offered as an alternative to water-based hair cleaning.

Dry shampoos contain, as essential active substance, a carrier material which is provided in the form of particles and which on account of its adsorption properties is able to bind contaminants located on the hair or the scalp, such as greases or sebum. In particular, optionally modified starches are used as carrier materials. If the hair is combed or brushed once the dry shampoo has been applied, the adsorbed contaminants will also be removed from the hair together with the powdery carrier material.

A preferred form of packaging for dry shampoos is an aerosol spray. In the case of corresponding products the powder suspended in a liquid phase is sprayed onto the hair by employing a propellant.

For many users of dry shampoos, in addition to a high cleaning performance, there is also a desire for additional styling effects, for example increased volume and/or improved hair texture, as a result of application of this shampoo, such that it is possible to do without the additional use of styling products. Styling effects of this kind can be achieved by the use of film-forming agents. However, the use of these film-forming agents can lead to a clogging of the aerosol spray, since the carrier material in the form of particles can clump together on account of the water introduced by the film-forming agent.

The object of the present disclosure was therefore to provide a dry shampoo having a high adsorption capacity and good application properties with regard to the application in the form of an aerosol spray, which shampoo, when used, leads to a high volume and/or improved hair texture, with these effects additionally having a very long-lasting effect. In addition, no visible residues or grey haze should remain on the hair after use.

BRIEF SUMMARY

In an exemplary embodiment, a cosmetic composition is provided and includes, in relation to the total weight of the cosmetic composition, a) at least one particle comprising, in relation to the total weight of the at least one particle, from about 65 to about 99% by weight of at least one native and/or physically modified starch, b) at least one anionic polymer comprising at least one structural unit of formula (I), at least one structural unit of formula (II), and at least one structural unit of formula (III):

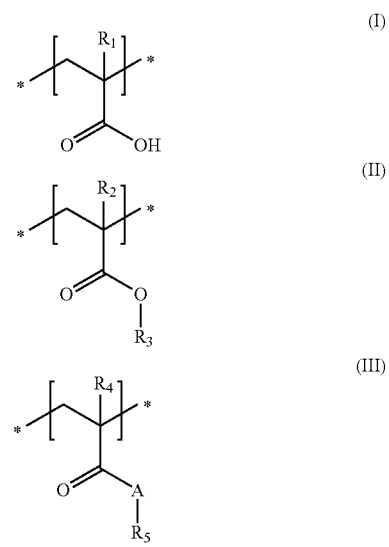

in which R1, R2 and R4, independently of one another, stand for a hydrogen atom or a C1-C4 alkyl group, R3 stands for a branched or unbranched, saturated or unsaturated C1-C12 alkyl group, R5 stands for a branched or unbranched, saturated or unsaturated C6-C14 alkyl group, and A stands for oxygen, sulfur or an NH group, and c) at least one propellant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has surprisingly been found that these objects can be achieved by a combination of starch in particle form as carrier material and a specific anionic polymer. This polymer is easily soluble in anhydrous solvents, but does not have to be neutralised for high film-forming properties. Consequently, by employing the use of this polymer, there is no undesirable introduction of water, which would lead to a clumping of the carrier material and thus to a clogging of the aerosol nozzle. Furthermore, this anionic polymer has a high resistance to water, and therefore the attained styling effects, in particular high volume and/or improved hair texture, are maintained over a long period of time, even if there is high relative humidity, or in event of exposure to water and sweat. In addition, this anionic polymer does not have a negative influence on the cleaning effect of the starch provided in particle form, and therefore, in addition to the high styling effect, excellent cleaning power can also be attained. In addition, this combination does not leave behind any visible residues or grey haze on the hair following application of the composition as contemplated herein.

A first subject of the present disclosure is therefore a cosmetic composition containing, in relation to its total weight,
a) at least one particle comprising, in relation to its total weight, from about 65 to about 99% by weight of at least one native and/or physically modified starch,
b) at least one anionic polymer, comprising at least one structural unit of formula (I) and at least one structural unit of formula (II) and at least one structural unit of formula (III)

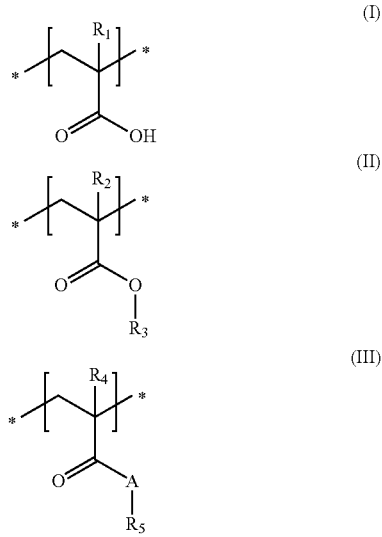

in which
R$_1$, R$_2$ and R$_4$, independently of one another, stand for a hydrogen atom or a C$_1$-C$_4$ alkyl group,
R$_3$ stands for a branched or unbranched, saturated or unsaturated C$_1$-C$_{12}$ alkyl group,
R$_5$ stands for a branched or unbranched, saturated or unsaturated C$_6$-C$_{14}$ alkyl group, and
A stands for oxygen, sulfur or an NH group, and
c) at least one propellant.

In accordance with the above formulas and all subsequent formulas, a chemical bond exemplified by the symbol "*" stands for a free valence of the corresponding structure fragment. Here, a "free valence" is understood to mean the number of atomic bonds emanating from the corresponding structure fragment in the position exemplified by the symbol "*". Within the scope of the present disclosure, an atomic bond preferably emanates from each of the positions of the structure fragments exemplified by the symbol "*" to further structure fragments.

The term "particle" will be understood to mean solids present in particulate form at about 25° C. and about 1,013 mbar.

Furthermore, a native starch is understood to mean a starch which is isolated from starch-containing plants and which, after isolation and purification, has been neither physically nor chemically modified. Starch is a reserve carbohydrate which is stored by many plants in the form of starch grains (granules), usually from about 1 μm to about 200 μm in size, in various plant parts, for example in tubers or roots, grain seeds, fruits, and in the pith. Starch belongs to the family of homoglycans and is a polycondensation product of D-glucose. Here, starch consists of three structurally different polymers of d-glucopyranose, specifically amylose, amylopectin, and what is known as an intermediate fraction.

By contrast, a physically modified starch is understood to mean a starch which has been subjected to at least one physical modification following the isolation. Here, physical modification is understood to mean modification under application of pressure and/or heat and/or light. A modification by employing chemical and enzymatic reactions, for example the hydrolysis of starch, however, does not fall under the term of physical modification. A physical modification used with preference is the application of heat, in particular the boiling of the native starch.

Within the scope of the present disclosure the term "anionic polymers" is understood to mean polymers which in a protic solvent under standard conditions carry at least one structural unit with permanently anionic groups, wherein the anionic groups have to be compensated for by counterions, thus resulting in electroneutrality. In particular, carboxyl groups are considered to fall under anionic groups as contemplated herein.

The specification of percent by weight in the present case, unless stated otherwise, relates to the total weight of the cosmetic composition as contemplated herein, wherein the sum of all ingredients of the composition as contemplated herein gives about 100% by weight.

As first essential constituent a), the cosmetic agent as contemplated herein contains at least one particle from native and/or physically modified starch. Starch particles that are preferred as contemplated herein are selected from at least one polycondensation product of D-glucose obtained from native and/or physically modified starch from potatoes, maize, rice, peas, acorns, chestnuts, barley, wheat, bananas, sago, millet, sorghum, oats, rye, beans, sweet potato, maranta or manioc, or mixtures thereof. With regard to the cleaning power, the use of native and/or physically modified rice starch has proven to be particularly advantageous. Preferred embodiments of the first subject matter of the present disclosure are therefore exemplified in that the at least one native and/or physically modified starch is selected from native and/or physically modified rice starches. The use of native and/or physically modified rice starches, in conjunction with the anionic polymer, leads not only to a high cleaning power of the cosmetic agents, but also ensures long-lasting styling effects, in particular high-volume and improved hair texture. In addition, no visible residues or grey haze remain on the hair once the hair has been cleaned.

It has been found as contemplated herein that the composition of the starch particles themselves is relevant for the cosmetic effect. Particles that are preferably used therefore comprise a specific proportion of the native and/or physically modified starch, in particular rice starch. It is thus preferred as contemplated herein if the at least one particle a) contains the at least one native and/or physically modified starch, in particular the native and/or physically modified rice starch, in a total amount of from about 70 to about 99% by weight, in particular from about 80 to about 95% by weight, in each case in relation to the total weight of the particle. The use of particles that contain a high proportion by weight of native and/or physically modified rice starch leads to a particularly high cleaning power of the cosmetic agents, but without negatively influencing the long-lasting styling effects attained by the anionic polymer, in particular the high volume and/or the improved hair texture.

Besides the native and/or physically modified starch, in particular rice starch, the particles can also contain further ingredients. Ingredients of this kind prevent the particles in the cosmetic agent from clumping together and thus clogging the aerosol nozzles, and therefore the container can be fully emptied. Cationic surfactants have proven to be particularly advantageous in this regard. A preferred embodiment of this subject of the present disclosure is therefore exemplified in that the at least one particle a) additionally contains at least one cationic surfactant, selected from the group of quaternary ammonium compounds, preferably from the group of cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, in particular from cetyltrimethylammonium chloride. The use of cetyltrimethylammonium chloride in the particles a), in particular on particles a) which contain the aforementioned proportions by weight of native and/or physically modified rice starch, leads to a high stability of these particles in the composition as contemplated herein. In this way, a clumping of the agent is avoided, and complete emptying of the aerosol container is ensured.

In this context, it is preferred if the at least one cationic surfactant, in particular cetyltrimethylammonium chloride, is contained within specific amount ranges in the particles a). It is therefore advantageous as contemplated herein if the at least one cationic surfactant, in particular cetyltrimethylammonium chloride, is contained in a total amount of from about 0.01 to about 1.0% by weight, in particular from about 0.05 to about 0.5% by weight, in each case in relation to the total weight of the particle.

With regard to the cleaning power and good application properties and the possibility for complete emptying of the container, it has proven to be advantageous if the particles a), in particular with the previously stated ingredients, have a specific mean particle size $D_{50}$. Preferred embodiments of the first subject of the present disclosure are therefore exemplified in that the at least one particle a) has a mean particle size $D_{50}$ of from about 0.5 μm to about 50 μm, preferably from about 0.2 μm to about 40 μm, preferably from about 4.0 μm to about 30 μm, in particular from about 5.0 μm to about 20 μm. The aforementioned mean particle sizes can be determined for example by employing dynamic light scattering (DLS).

Particles a) that are used with particular preference are therefore exemplified in that they contain in relation to their total weight
from about 80 to about 95% by weight of a native and/or physically modified rice starch, and
from about 0.05 to about 0.5% by weight of cetyltrimethylammonium chloride.

Further particles a) that are used with particular preference are exemplified in that they contain, in relation to their total weight
from about 80 to about 95% by weight of a native and/or physically modified rice starch and
from about 0.05 to about 0.5% by weight of cetyltrimethylammonium chloride and have a mean particle diameter $D_{50}$ of from about 5.0 μm to about 20 μm.

Preferred cosmetic compositions as contemplated herein contain the at least one particle a) in a total amount of from about 1.0 to about 10% by weight, preferably from about 1.0 to about 8.0% by weight, preferably from about 1.5 to about 6.0% by weight, in particular from about 1.5 to about 5.0% by weight, in each case in relation to the total weight of the composition. The use of the aforementioned total amount of particles a), in particular of particles a) having the aforementioned properties, has proven to be advantageous in particular in respect of the application properties and cleaning power. Furthermore, the use of these total amounts does not negatively influence the long-lasting styling effect attained by the anionic polymer b), in particular the high volume and/or the improved texture. In addition, no visible residues or grey haze remain on the hair with use of the aforementioned total amounts.

As second essential constituent b), the cosmetic agent as contemplated herein contains at least one anionic polymer which contains at least one structural unit of formulas (I) to (III). In the structural units of formulas (I) to (III) the groups $R_1$, $R_2$ and $R_4$ stand for $C_1$-$C_4$ alkyl groups. Examples of groups of this kind are methyl, ethyl, propyl, isopropyl, hydroxypropyl, butyl, sec-butyl, isobutyl, tert-butyl and hydroxybutyl groups. Furthermore, the groups $R_3$ and $R_5$ in the structural units of formulas (II) and (III) can stand for $C_1$-$C_{12}$ or $C_6$-$C_{14}$ alkyl groups. Groups of this kind are, for example, pentyl, hexyl, heptyl, capryl, caprin, lauryl and myristyl groups.

Within the scope of the present disclosure it is preferable if the groups $R_1$, $R_2$ and $R_4$ in formulas (I) to (III) stand for specific groups. Preferred embodiments of this subject matter of the present disclosure are therefore exemplified in that, in the structural units of formulas (I) and (III), the groups $R_1$ and $R_4$, independently of one another, stand for a hydrogen atom and in that, in the structural unit of formula (II), the group $R_2$ stands for a methyl group. Anionic polymers based on acrylic acid, methacrylates and acrylamides or acrylates are therefore preferably used. The use of anionic polymers of this kind leads to a particularly high water resistance of the styling effects attained.

It has also proven to be advantageous within the scope of the present disclosure if the group $R_3$ in the structural unit of formula (II) stands for specific groups. It is therefore preferred that in the structural unit of formula (II) the group $R_3$ stands for a branched $C_3$-$C_6$ alkyl group, in particular for a *—$CH_2$—$CH(CH_3)_2$ group. Here, the * symbol indicates the linking of the group $R_3$ to the oxygen atom of the structural unit of formula (II). The group $R_3$ is thus bound to the carbonyl group of the structural group of formula (II) via the $CH_2$ group. The use of anionic polymers which in particular contain branched methacrylates has proven to be particularly advantageous in respect of the water resistance of the styling effects attained.

It is also preferred as contemplated herein if, in the structural unit of formula (III), A stands for an NH group. Preferred anionic polymers therefore contain at least one structural unit based on acrylamides. The use of anionic polymers based on acrylamides leads to an improved resistance to external ambient influences, but without negatively influencing the cleaning power of the particles a).

It has additionally proven to be advantageous within the scope of the present disclosure if the group $R_5$ in the structural unit of formula (III) stands for specific groups. It is therefore preferred as contemplated herein if, in the structural unit of formula (III), the group $R_5$ stands for a branched $C_6$-$C_{10}$ alkyl group, in particular for a *—$C(CH_3)_2$—$CH_2$—$C(CH_3)_3$ group. Here, the * symbol indicates the linking of the group $R_5$ to the unit A of the structural unit of formula (III). The use of anionic polymers which in particular contain branched acrylamides and acrylates has proven to be particularly advantageous in respect of the water resistance of the styling effects attained.

Anionic polymers which contain at least one structural unit of formula (I), at least one structural unit of formula (II), and at least one structural unit of formula (III)

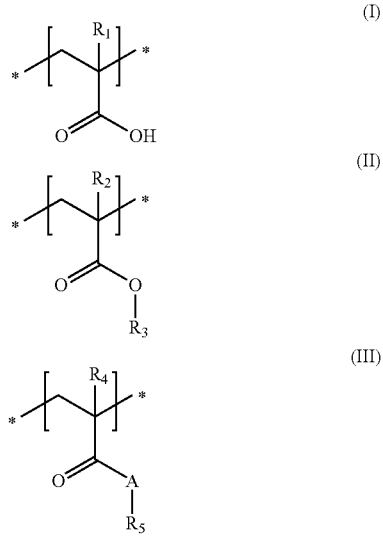

in which
R$_1$ and R$_4$ each stand for a hydrogen atom,
R$_2$ stands for a methyl group
R$_3$ stands for a *—CH$_2$—CH(CH$_3$)$_2$ group,
R$_5$ stands for a *—C(CH$_3$)$_2$—CH$_2$—C(CH$_3$)$_3$ group, and
A stands for an NH group
are therefore used with particular preference as contemplated herein.

The use of anionic polymers of this kind based on acrylic acid, 2-methylpropylmethacrylate and octylacrylamide has proven to be particularly advantageous in respect of the resistance of the attained styling effects to external ambient influences. The combination of particles a), in particular the aforementioned specific particles a), with the specific anionic polymers b) leads not only to a high cleaning power, but also to long-lasting and water-resistant styling effects, in particular increased volume and improved hair texture. In addition, no visible residues or grey haze remain on the hair following the application of this combination.

Anionic polymers used with preference have specific mean molecular weights M$_w$. These molecular weights can be determined for example by coupling gel permeation chromatography (GPC) with Fourier transform mass spectrometry (FTMS), as described in Aaserud D. J et. al; "Gel Permeation Chromatography Coupled to Fourier Transform Mass Spectrometry for Polymer Characterization"; Anal. Chem. 1999, 71, 4793-4799. Preferred embodiments of this subject of the present disclosure are therefore exemplified in that the anionic polymer has a mean molecular weight M$_w$ of from about 50,000 g/mol to about 250,000 g/mol, preferably from about 80,000 g/mol to about 220,000 g/mol, preferably from about 100,000 g/mol to about 200,000 g/mol, in particular from about 110,000 g/mol to about 180,000 g/mol.

Preferred cosmetic agents as contemplated herein contain the at least one anionic polymer b) in a total amount of from about 1.0 to about 8.0% by weight, preferably from about 1.5 to about 7.0% by weight, preferably from about 1.5 to about 6.0% by weight, in particular from about 1.5 to about 5.0% by weight, in relation to the total weight of the composition. The use of these amounts of the anionic polymer results in a long-lasting and water-resistant styling effect, but without negatively influencing the cleaning power, and without leading to a clumping of the used particles and thus a clogging of the aerosol nozzle and without leaving behind visible residues or a grey haze on the hair after application.

As third essential constituent c), the cosmetic agent as contemplated herein contains at least one propellant. All gases permitted for use in cosmetic agents can be used in principle as propellant. The use of specific gases, however, has proven to be advantageous in respect of the complete emptying of the aerosol container. Preferred embodiments of the first subject of the present disclosure are therefore exemplified in that the at least one propellant c) is selected from the group of propane, propane/butane mixtures and dimethyl ether, in particular from the group of propane/butane mixtures.

In order to ensure good applicability and so as to be able to apply a sufficient amount of the composition to the hair, it has proven to be advantageous if the propellant is used within certain amount ranges. It is therefore preferred as contemplated herein if the composition contains the at least one propellant c), in particular propane/butane mixtures, in a total amount of from about 80 to about 96% by weight, preferably from about 82 to about 94% by weight, preferably from about 84 to about 93% by weight, in particular from about 86 to about 92% by weight, in each case in relation to the total weight of the composition.

In order to avoid a clogging of the aerosol nozzles on account of a clumping of the particles a) with introduction of water, it is particularly preferred as contemplated herein if the composition does not contain any basic compounds for neutralisation of the anionic polymer b). The term "basic compounds" as contemplated herein means all compounds that are able to form hydroxide ions in water or to act as proton acceptors. The term includes in particular alkali and alkaline earth metal hydroxides, alkali and alkaline earth metal carbonates, ammonia, and organic amines. This is because, with neutralisation of this polymer by basic compounds, water is released or introduced and leads to a clumping of the particles a) and thus to a clogging of the aerosol nozzle. Consequently, complete emptying of the container is no longer possible. As contemplated herein, "no basic compounds" means that these are contained in a total amount of about 0% by weight in relation to the total weight of the composition. Particularly preferred embodiments of the first subject of the present disclosure are therefore exemplified in that the composition does not contain any basic compounds, in particular no organic amines and/or hydroxides.

The clogging of the aerosol nozzle can likewise be avoided if the compositions as contemplated herein contain merely a small amount of water and if an anhydrous organic solvent is used as solvent for the anionic polymer. A clumping of the particles a) is hereby avoided, which would lead to a clogging of the nozzle and would prevent complete emptying of the aerosol container. Particularly preferred compositions thus contain water in a total amount of from about 0 to about 2.0% by weight, preferably from about 0 to about 1.5% by weight, preferably from about 0 to about 1.0% by weight, in particular from about 0 to about 0.99% by weight, in each case in relation to the total weight of the composition. Consequently, the propellant c) and the anhydrous solvent for the anionic polymer b) are used as carriers for the ingredients of the composition as contemplated herein.

The anionic polymer b) is preferably dissolved in organic solvents in order to ensure that the composition can be distributed uniformly over the hair when it is applied and in this way can attain long-lasting and water-resistant styling effects. In order to reduce the introduction of water and thus the risk of clumping of the particles a), an organic solvent is preferably used. It is therefore preferred as contemplated herein if the composition additionally contains ethanol in a total amount of from about 3.0 to about 8.0% by weight, in particular from about 4.0 to about 6.0% by weight, in relation to the total weight of the composition. The aforementioned amount on the one hand is sufficient to dissolve the anionic polymer b) and to ensure uniform distribution over the hair. On the other hand this amount does not lead to excessive moistening of the hair, such that a dry cleaning of the hair is made possible.

Particularly preferred embodiments AF 1 to AF 72 of the cosmetic compositions as contemplated herein are specified in the following tables (all values in % by weight).

|  | AF 1 | AF 2 | AF 3 | AF 4 |
|---|---|---|---|---|
| Particle a) | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |

|  | AF 5 | AF 6 | AF 7 | AF 8 |
|---|---|---|---|---|
| Particle a) [1] | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |

|  | AF 9 | AF 10 | AF 11 | AF 12 |
|---|---|---|---|---|
| Particle a) [2] | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |

|  | AF 13 | AF 14 | AF 15 | AF 16 |
|---|---|---|---|---|
| Particle a) [3] | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant Pc) | 80 to 96 | 82 to 94 | 84 to 93 | 86 to 92 |

|  | AF 17 | AF 18 | AF 19 | AF 20 |
|---|---|---|---|---|
| Particle a) | 1.0 to 10 | 1.0 to 8.0 | 1.5 to 6.0 | 1.5 to 5.0 |
| Anionic polymer b) [4] | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |

|  | AF 21 | AF 22 | AF 23 | AF 24 |
|---|---|---|---|---|
| Particle a) | 1.0 to 10 | 1.0 to 8.0 | 1.5 to 6.0 | 1.5 to 5.0 |
| Anionic polymer b) [5] | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |

|  | AF 25 | AF 26 | AF 27 | AF 28 |
|---|---|---|---|---|
| Particle a) | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) [6] | 80 to 96 | 82 to 94 | 84 to 93 | 86 to 92 |

|  | AF 29 | AF 30 | AF 31 | AF 32 |
|---|---|---|---|---|
| Particle a) [1] | 1.0 to 10 | 1.0 to 8.0 | 1.5 to 6.0 | 1.5 to 5.0 |
| Anionic polymer b) [4] | 1.0 to 8.0 | 1.5 to 7.0 | 1.5 to 6.0 | 1.5 to 5.0 |
| Propellant c) [6] | 80 to 96 | 82 to 94 | 84 to 93 | 86 to 92 |

|  | AF 33 | AF 34 | AF 35 | AF 36 |
|---|---|---|---|---|
| Particle a) [3] | 1.0 to 10 | 1.0 to 8.0 | 1.5 to 6.0 | 1.5 to 5.0 |
| Anionic polymer b) [5] | 1.0 to 8.0 | 1.5 to 7.0 | 1.5 to 6.0 | 1.5 to 5.0 |
| Propellant c) [6] | 80 to 96 | 82 to 94 | 84 to 93 | 86 to 92 |

|  | AF 37 | AF 38 | AF 39 | AF 40 |
|---|---|---|---|---|
| Particle a) | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |
| Water | 0 to 2.0 | 0 to 1.5 | 0 to 1.0 | 0 to 0.99 |

|  | AF 41 | AF 42 | AF 43 | AF 44 |
|---|---|---|---|---|
| Particle a) [1] | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |
| Water | 0 to 2.0 | 0 to 1.5 | 0 to 1.0 | 0 to 0.99 |

|  | AF 45 | AF 46 | AF 47 | AF 48 |
|---|---|---|---|---|
| Particle a) [2] | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |
| Water | 0 to 2.0 | 0 to 1.5 | 0 to 1.0 | 0 to 0.99 |

|  | AF 49 | AF 50 | AF 51 | AF 52 |
|---|---|---|---|---|
| Particle a) [3] | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |
| Water | 0 to 2.0 | 0 to 1.5 | 0 to 1.0 | 0 to 0.99 |

|  | AF 53 | AF 54 | AF 55 | AF 56 |
|---|---|---|---|---|
| Particle a) | 1.0 to 10 | 1.0 to 8.0 | 1.5 to 6.0 | 1.5 to 5.0 |
| Anionic polymer b) [4] | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |
| Water | 0 to 2.0 | 0 to 1.5 | 0 to 1.0 | 0 to 0.99 |

|  | AF 57 | AF 58 | AF 59 | AF 60 |
|---|---|---|---|---|
| Particle a) | 1.0 to 10 | 1.0 to 8.0 | 1.5 to 6.0 | 1.5 to 5.0 |
| Anionic polymer b) [5] | 1.0 to 8.0 | 1.5 to 7.0 | 1.5 to 6.0 | 1.5 to 5.0 |
| Propellant c) | 80 to 96 | 82 to 94 | 84 to 93 | 86 to 92 |
| Water | 0 to 2.0 | 0 to 1.5 | 0 to 1.0 | 0 to 0.99 |

|  | AF 61 | AF 62 | AF 63 | AF 64 |
|---|---|---|---|---|
| Particle a) | 1.0 to 10 | 1.0 to 8.0 | 1.5 to 6.0 | 1.5 to 5.0 |
| Anionic polymer b) | 1.0 to 8.0 | 1.5 to 7.0 | 1.5 to 6.0 | 1.5 to 5.0 |
| Propellant c) [6] | 80 to 96 | 82 to 94 | 84 to 93 | 86 to 92 |
| Water | 0 to 2.0 | 0 to 1.5 | 0 to 1.0 | 0 to 0.99 |

|  | AF 65 | AF 66 | AF 67 | AF 68 |
|---|---|---|---|---|
| Particle a) [1] | 1.0 to 10 | 1.0 to 8.0 | 1.5 to 6.0 | 1.5 to 5.0 |
| Anionic polymer b) [4] | 1.0 to 8.0 | 1.5 to 7.0 | 1.5 to 6.0 | 1.5 to 5.0 |
| Propellant c) [6] | 80 to 96 | 82 to 94 | 84 to 93 | 86 to 92 |
| Water | 0 to 2.0 | 0 to 1.5 | 0 to 1.0 | 0 to 0.99 |

|  | AF 69 | AF 70 | AF 71 | AF 72 |
|---|---|---|---|---|
| Particle a) [3] | 1.0 to 10 | 1.0 to 8.0 | 1.5 to 6.0 | 1.5 to 5.0 |
| Anionic polymer b) [5] | 1.0 to 8.0 | 1.5 to 7.0 | 1.5 to 6.0 | 1.5 to 5.0 |
| Propellant c) [6] | 80 to 96 | 82 to 94 | 84 to 93 | 86 to 92 |
| Water | 0 to 2.0 | 0 to 1.5 | 0 to 1.0 | 0 to 0.99 |

[1] containing from about 80 to about 95% by weight, in relation to the total weight of the Particle a), of native and/or physically modified rice starch,
[2] containing from about 80 to about 95% by weight, in relation to the total weight of the Particle a), of native and/or physically modified rice starch, and cetyltrimethylammonium chloride,
[3] containing from about 80 to about 95% by weight, in relation to the total weight of the Particle a), of native and/or physically modified rice starch, and from about 0.05 to about 0.5% by weight, in relation to the total weight of the Particle a), of cetyltrimethylammonium chloride,
[4] containing structural units of formulas (I) to (III), where $R_1$, $R_2$ and $R_4$ in each case = H or $C_1$-$C_4$ alkyl group, $R_3$ = branched or unbranched, saturated or unsaturated $C_1$-$C_{12}$ alkyl group, $R_5$ = branched or unbranched, saturated or unsaturated $C_6$-$C_{14}$ alkyl group, A = O, S or NH,
[5] containing structural units of formulas (I) to (III), where $R_1$, $R_4$ in each case = H, $R_2$ = methyl group, $R_3$ = *—$CH_2$—$C(CH_3)_2$ group, $R_5$ = *—$C(CH_3)_2$—$CH_2$—$C(CH_3)_3$ group, A = NH
[6] selected from propane/butane mixtures.

Embodiments AF 1 to AF 72 contain water in a total amount of from about 0 to about 0.99% by weight in relation to the total weight of the composition, and preferably contain about 0% by weight, in relation to the total weight of the embodiment in question, of basic compounds, in particular of organic amines and/or hydroxides. By the use of specific particles a) in conjunction with specific anionic polymers b), these embodiments have a high cleaning effect and, after the cleaning, lead to long-lasting and water-resistant styling effects, in particular increased hair volume and/or improved hair texture. The use of further styling products once the hair has been cleaned with use of these dry shampoos can thus be avoided. Since the anionic polymer b) does not have to be neutralised and is soluble in organic solvents, the amount of water in these embodiments can be reduced and therefore a clumping of the particles a) can be avoided. These embodiments can thus be emptied fully from aerosol containers, since a clogging of the nozzles caused by the clumping of the particles a) is avoided. In addition, the application properties and the cleaning power are improved hereby, since uniform application of the particles a) to the hair is ensured. Embodiments AF 1 to AF 72 also do not leave behind any visible residues or grey haze on the hair after application.

Besides the above-described components, the cosmetic compositions as contemplated herein can contain further ingredients, in particular additional nourishing substances.

As nourishing substance, the composition can contain at least one protein hydrolysate and/or a derivative thereof, for example. Protein hydrolysates are product mixtures that are obtained by acid-, base- or enzyme-catalysed degradation of proteins. The term "protein hydrolysates" as contemplated herein also means total hydrolysates and individual amino acids and derivatives thereof and mixtures of various amino acids. The molar mass of the protein hydrolysates that can be used as contemplated herein lies between about 75 daltons, the molar mass for glycine, and about 200,000 daltons, with the molar mass preferably being from about 75 daltons to about 50,000 daltons and very particularly preferably from about 75 daltons to about 20,000 daltons.

At least one vitamin, a provitamin, a vitamin precursor and/or one of the derivatives thereof can also be contained as nourishing substance. Here, vitamins, provitamins and vitamin precursors which are usually assigned to groups A, B, C, E, F and H are preferred as contemplated herein.

Further suitable nourishing substances are for example panthenol, caffeine, nicotinamide, sorbitol, and mixtures thereof.

The compositions as contemplated herein can additionally contain at least one plant extract, but also mono- or oligosaccharides and/or lipids as nourishing substance.

The cosmetic compositions as contemplated herein are preferably used as dry shampoos for cleaning the hair, whilst also attaining long-lasting styling effects.

A second subject matter of the present disclosure is therefore the use of a cosmetic composition as contemplated herein for cleaning keratin fibres, in particular human hair.

The term "keratin fibres" is understood to mean, in principle, all animal hair, for example wool, horsehair, angora hair, fur, feathers, and products or textiles made therefrom. The keratin fibres, however, are preferably human hair.

That which has been said with regard to the compositions as contemplated herein also applies, mutatis mutandis, with regard to further preferred embodiments of the method as contemplated herein, in particular with regard to the cosmetic composition used there.

A third subject of the present disclosure is a method for cleaning keratin fibres, in particular human hair, in which the cosmetic composition as contemplated herein is applied to keratin fibres.

In order to clean keratin fibres, the cosmetic composition is applied to the fibres. In a further step the composition can then be removed again from the keratin fibres, at least in part. This can be achieved for example by mechanical action on the fibres, in particular by combing or brushing the fibres. Alternatively, the cosmetic composition can also be blown out of the hair, for example by employing a hairdryer.

If the cosmetic composition is at least partially removed again from the keratin fibres after the application, the period of time for which the composition acts on the fibres is thus preferably between about 1 minute and about 10 minutes.

A preferred embodiment of this subject of the present disclosure is therefore a method in which the cosmetic composition is left on the hair after application or is removed from the hair at least partially, in particular completely, after application.

A fundamental advantage of the method as contemplated herein lies in cleaning the hair and at the same time attaining long-lasting water-resistant styling effects, but without leaving behind visible residues or a grey haze on the hair after application. This is achieved by the combination of the particles a) and anionic polymer b) described previously in conjunction with the first subject.

That which has been said with regard to the compositions as contemplated herein and the use as contemplated herein also applies, mutatis mutandis, with regard to further preferred embodiments of the method as contemplated herein, in particular with regard to the cosmetic composition used there.

The subject matter of the present disclosure is exemplified in particular by the following points:

1. A cosmetic composition, containing, in relation to its total weight,
    a) at least one particle comprising, in relation to its total weight, from about 65 to about 99% by weight of at least one native and/or physically modified starch,
    b) at least one anionic polymer, comprising at least one structural unit of formula (I) and at least one structural unit of formula (II) and at least one structural unit of formula (III)

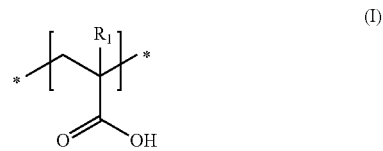

(I)

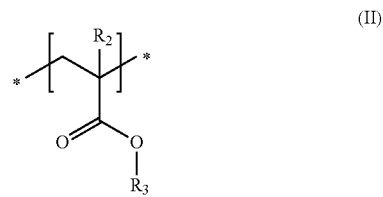

(II)

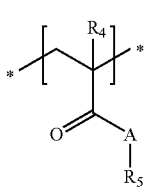

in which

R₁, R₂ and R₄, independently of one another, stand for a hydrogen atom or a $C_1$-$C_4$ alkyl group, R₃ stands for a branched or unbranched, saturated or unsaturated $C_1$-$C_{12}$ alkyl group, R₅ stands for a branched or unbranched, saturated or unsaturated $C_6$-$C_{14}$ alkyl group, and A stands for oxygen, sulfur or an NH group, and c) at least one propellant.

2. The cosmetic composition according to point 1, exemplified in that the at least one native and/or physically modified starch is selected from native and/or physically modified rice starches.

3. The cosmetic composition according to either one of points 1 or 2, exemplified in that the at least one particle a) contains the at least one native and/or physically modified starch, in particular the native and/or physically modified rice starch, in a total amount of from about 70 to about 99% by weight, in particular from about 80 to about 95% by weight, in each case in relation to the total weight of the particle.

4. The cosmetic composition according to any one of the preceding points, exemplified in that the at least one particle a) additionally contains at least one cationic surfactant, selected from the group of cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, in particular from cetyltrimethylammonium chloride.

5. The cosmetic composition according to point 4, exemplified in that the at least one cationic surfactant, in particular cetyltrimethylammonium chloride, is contained in a total amount of from about 0.01 to about 1.0% by weight, in particular from about 0.05 to about 0.5% by weight, in each case in relation to the total weight of the particle.

6. The cosmetic agent according to any one of the preceding points, exemplified in that the at least one particle a) has a mean particle size $D_{50}$ of from about 0.5 μm to about 50 μm, preferably from about 2.0 μm to about 40 μm, preferably from about 4.0 μm to about 30 μm, in particular from about 5.0 μm to about 20 μm.

7. The cosmetic composition according to any one of the preceding points, exemplified in that the composition contains the at least one particle a) in a total amount of from about 1.0 to about 10% by weight, preferably from about 1.0 to about 8.0% by weight, preferably from about 1.5 to about 6.0% by weight, in particular from about 1.5 to about 5.0% by weight, in each case in relation to the total weight of the composition.

8. The cosmetic composition according to any one of the preceding points, exemplified in that, in the structural units of formulas (I) and (III), the groups R₁ and R₄, independently of one another, stand for a hydrogen atom, and in that, in the structural unit of formula (II), the group R₂ stands for a methyl group.

9. The cosmetic composition according to any one of the preceding points, exemplified in that, in the structural unit of formula (II), the group R₃ stands for a branched $C_3$-$C_6$ alkyl group, in particular for a *—$CH_2$—$CH(CH_3)_2$ group.

10. The cosmetic composition according to any one of the preceding points, exemplified in that, in the structural unit of formula (III), A stands for an NH group.

11. The cosmetic composition according to any one of the preceding points, exemplified in that, in the structural unit of formula (III), the group R₅ stands for a branched $C_6$-$C_{10}$ alkyl group, in particular for a *—$C(CH_3)_2$—$CH_2$—$C(CH_3)_3$ group.

12. The cosmetic composition according to any one of the preceding points, exemplified in that the at least one anionic polymer b) has a mean molecular weight $M_w$ of from about 50,000 g/mol to about 250,000 g/mol, preferably from about 80,000 g/mol to about 220,000 g/mol, preferably from about 100,000 g/mol to about 200,000 g/mol, in particular from about 110,000 g/mol to about 180,000 g/mol.

13. The cosmetic composition according to any one of the preceding points, exemplified in that the composition contains the at least one anionic polymer b) in a total amount of from about 1.0 to about 8.0% by weight, preferably from about 1.5 to about 7.0% by weight, preferably from about 1.5 to about 6.0% by weight, in particular from about 1.5 to about 5.0% by weight, in relation to the total weight of the composition.

14. The cosmetic composition according to any one of the preceding points, exemplified in that the at least one propellant c) is selected from the group of propane, propane/butane mixtures, and dimethyl ether, in particular from the group of propane/butane mixtures.

15. The cosmetic composition according to any one of the preceding points, exemplified in that the composition contains the at least one propellant c), in particular propane/butane mixtures, in a total amount of from about 80 to about 96% by weight, preferably from about 82 to about 94% by weight, preferably from about 84 to about 93% by weight, in particular from about 86 to about 92% by weight, in each case in relation to the total weight of the composition.

16. The cosmetic composition according to any one of the preceding points, exemplified in that the composition does not contain any basic compounds, in particular no organic amines and/or hydroxides.

17. The cosmetic composition according to any one of the preceding points, exemplified in that the composition contains water in a total amount of from about 0 to about 2.0% by weight, preferably from about 0 to about 1.5% by weight, preferably from about 0 to about 1.0% by weight, in particular from about 0 to about 0.99% by weight, in each case in relation to the total weight of the composition.

18. The cosmetic composition according to any one of the preceding points, exemplified in that the composition additionally contains ethanol in a total amount of from about 3.0 to about 8.0% by weight, in particular from about 4.0 to about 6.0% by weight, in relation to the total weight of the composition.

19. Use of a cosmetic composition according to any one of points 1 to 18 for cleaning keratin fibres, in particular human hair.

20. A method for cleaning keratin fibres, in particular human hair, in which the cosmetic composition according to any one of points 1 to 18 is applied to keratin fibres.

21. The method according to point 20, wherein the cosmetic composition is left on the hair after application or is removed from the hair at least partially, in particular fully, after application.

The following examples explain the present disclosure, but are not intended to be limiting:

EXAMPLES

The following aerosol composition was produced:

|   | Raw material | % by weight |
|---|---|---|
| 1 | Ethanol 99% denat | 7.0 |
| 2 | Particles a) [1] | 4.0 |
| 3 | Anionic polymer [2] | 3.0 |
| 4 | Perfume | 0.2 |
| 5 | Propane/butane (15:85) | 85.8 |

[1] containing from about 80 to about 95% by weight, in relation to the total weight of the particle a), of native and/or modified rice starch, and from about 0.05 to about 0.5% by weight, in relation to the total weight of the particle a), of cetyltrimethylammonium chloride,
[2] containing structural units of formulas (I) to (III), where $R_1$, $R_4$ in each case = H, $R_2$ = methyl group, $R_3$ = *—$CH_2$—$C(CH_3)_2$ group, $R_5$ = *—$C(CH_3)_2$—$CH_2$—$C(CH_3)_3$ group, A = NH The composition was produced by mixing raw materials 1 to 4, filling these into an aerosol can, and applying an appropriate amount of the propellant (raw material 5) to this can. The composition had good application properties and excellent cleaning power after having been applied to the hair and brushed out. Furthermore, increased volume and improved hair texture were noted after the cleaning, without the treated hair showing any visible residues or grey haze. Even after a longer period of storage, no clogging of the aerosol nozzle was observed, and the composition could be emptied fully from the container.

The invention claimed is:

1. A cosmetic composition comprising,
   a) particles comprising, in relation to the total weight of the particles, from 65 to 99% by weight of at least one native and/or physically modified starch, wherein the particles have a mean particle diameter of from 0.5 microns to 50 microns as measured by dynamic light scattering,
   b) at least one anionic polymer comprising at least one structural unit of formula (I), at least one structural unit of formula (II), and at least one structural unit of formula (III):

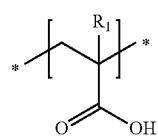

(I)

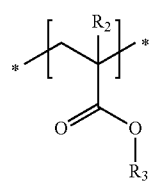

(II)

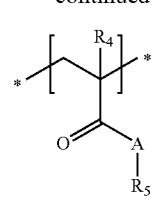

(III)

in which
$R_1$, $R_2$ and $R_4$, independently of one another, stand for a hydrogen atom or a $C_1$-$C_4$ alkyl group,
$R_3$ stands for a branched or unbranched, saturated or unsaturated $C_1$-$C_{12}$ alkyl group,
A stands for oxygen, sulfur or an NH group, and wherein when A stand for oxygen, $R_5$ stands for a branched or unbranched, saturated unsaturated $C_{13}$-$C_{14}$ alkyl group, and wherein when A stands for sulfur or an NH group, $R_5$ stands for a branched or unbranched, saturated or unsaturated $C_6$-$C_{14}$ alkyl group, and
   c) at least one propellant, wherein the cosmetic composition is free of chemically modified starch.

2. The cosmetic composition according to claim 1, wherein the at least one native and/or physically modified starch is selected from native and/or physically modified rice starches.

3. The cosmetic composition according to claim 1, wherein the particles a) comprise the at least one native and/or physically modified starch in a total amount of from 70% to 99% by weight in relation to the total weight of the particles.

4. The cosmetic composition according to claim 1, wherein the cosmetic composition comprises the particles a) in a total amount of from 1.0% to 10% by weight in relation to the total weight of the cosmetic composition.

5. The cosmetic composition according to claim 1, wherein, in the structural unit of formula (II), the group $R_3$ stands for a branched $C_3$-$C_6$ alkyl group.

6. The cosmetic composition according to claim 1, wherein, in the structural unit of formula (III), the group $R_5$ stands for a branched $C_6$-$C_{10}$ alkyl group.

7. The cosmetic composition according to claim 1, wherein the cosmetic composition comprises the at least one anionic polymer b) in a total amount of from 1.0% to 8.0% by weight in relation to the total weight of the cosmetic composition.

8. The cosmetic composition according to claim 1, wherein the cosmetic composition comprises the at least one propellant c) in a total amount of from 80% to 96% by weight in relation to the total weight of the cosmetic composition.

9. A method for cleaning keratin fibres in which the cosmetic composition according to claim 1 is applied to keratin fibres.

10. The cosmetic composition according to claim 1, wherein, in the structural unit of formula (II), the group $R_3$ stands for a *—$CH_2$—$CH(CH_3)_2$ group.

11. The cosmetic composition according to claim 1, wherein, in the structural unit of formula (III), the group $R_5$ stands for a *—$C(CH_3)_2$—$CH_2$—$C(CH_3)_3$ group.

12. The cosmetic composition according to claim 1, wherein the at least one propellant c) is a propane/butane mixture, and wherein the cosmetic composition comprises the at least one propellant c) in a total amount of from 80% to 96% by weight in relation to the total weight of the cosmetic composition.

13. The cosmetic composition according to claim 1, wherein the particles a) further comprise at least one cationic surfactant.

14. The cosmetic composition according to claim 13, wherein the at least one cationic surfactant, in relation to the total weight of the particles a), is present in an amount of from 0.01% to 1.0% by weight.

15. The cosmetic composition according to claim 14, wherein the at least one cationic surfactant is selected from the group of cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride.

16. The cosmetic composition according to claim 15, wherein the at least one cationic surfactant is cetyltrimethylammonium chloride.

17. The cosmetic composition according to claim 16, wherein the at least one cationic surfactant, in relation to the total weight of the particles a), is present in an amount of from 0.05% to 0.5% by weight.

18. The cosmetic composition according to claim 1, wherein the mean particle diameter of the particles a) is from 5.0 microns to 20 microns as measured by dynamic light scattering.

19. A cosmetic composition consisting of, in relation to the total weight of the cosmetic composition,
   a) particles present in a total amount of from 1.0% to 10% by weight and consisting of, in relation to the total weight of the particles,
      from 65% to 99% by weight of at least one native and/or physically modified starch, wherein the particles have a mean particle diameter of from 0.5 microns to 50 microns as measured by dynamic light scattering, and
      from 0.01% to 1.0% by weight of at least one cationic surfactant,
   b) at least one anionic polymer that is present in a total amount of from 1.0% to 8.0% by weight and that comprising at least one structural unit of formula (I), at least one structural unit of formula (II), and at least one structural unit of formula (III):

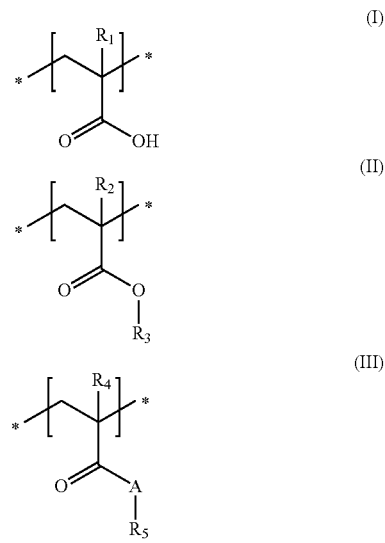

in which
$R_1$, $R_2$ and $R_4$, independently of one another, stand for a hydrogen atom or a $C_1$-$C_4$ alkyl group,
$R_3$ stands for a branched or unbranched, saturated or unsaturated $C_1$-$C_{12}$ alkyl group,
A stands for oxygen, sulfur or an NH group, and wherein when A stand for oxygen, $R_5$ stands for a branched or unbranched, saturated unsaturated $C_{13}$-$C_{14}$ alkyl group, and wherein when A stands for sulfur or an NH group, $R_5$ stands for a branched or unbranched, saturated or unsaturated $C_6$-$C_{14}$ alkyl group,
   c) at least one propellant present in a total amount of from 80% to 96% by weight,
   d) water that is present in a total amount of from 0 to 2.0% by weight,
   e) optionally at least one organic solvent that, if present, is in a total amount of from 3.0% to 8.0% by weight, and
   f) optionally at least one nourishing substance selected from the group of protein hydrolysates, vitamins, provitamins, vitamin precursors, panthenol, caffeine, nicotinamide, sorbitol, plant extracts, monosaccharides, oligosaccharides, and lipids.

* * * * *